United States Patent
Zhu

(10) Patent No.: US 10,765,093 B2
(45) Date of Patent: Sep. 8, 2020

(54) HUMANIZED TRANSGENIC ANIMAL

(76) Inventor: James Zhu, Cupertino, CA (US)

(*) Notice: Subject to any disclaimer, the term of this patent is extended or adjusted under 35 U.S.C. 154(b) by 194 days.

(21) Appl. No.: 13/989,781

(22) PCT Filed: Nov. 28, 2011

(86) PCT No.: PCT/US2011/062272
§ 371 (c)(1),
(2), (4) Date: May 24, 2013

(87) PCT Pub. No.: WO2012/071592
PCT Pub. Date: May 31, 2012

(65) Prior Publication Data
US 2013/0254907 A1  Sep. 26, 2013

Related U.S. Application Data

(60) Provisional application No. 61/417,411, filed on Nov. 27, 2010.

(51) Int. Cl.
| A01K 67/027 | (2006.01) |
| C12N 15/85 | (2006.01) |
| C07K 14/52 | (2006.01) |
| C07K 14/535 | (2006.01) |
| C07K 14/71 | (2006.01) |
| C07K 14/715 | (2006.01) |
| A61K 49/00 | (2006.01) |

(52) U.S. Cl.
CPC ...... A01K 67/0278 (2013.01); A61K 49/0008 (2013.01); C07K 14/52 (2013.01); C07K 14/535 (2013.01); C07K 14/71 (2013.01); C07K 14/715 (2013.01); C12N 15/8509 (2013.01); A01K 2217/072 (2013.01); A01K 2217/15 (2013.01); A01K 2227/105 (2013.01); A01K 2267/03 (2013.01)

(58) Field of Classification Search
CPC ............ A01K 67/0278; A01K 49/0008; A01K 2217/072; A01K 2227/105; A01K 2267/03; A01K 2217/15; C07K 14/715; C07K 14/52; C07K 14/535; C07K 14/71; C12N 15/8509
USPC .................................. 800/13, 18, 3; 530/351
See application file for complete search history.

(56) References Cited

U.S. PATENT DOCUMENTS

| 7,919,670 | B1* | 4/2011 | Stern ................. A01K 67/0275 800/18 |
| 2002/0066117 | A1 | 5/2002 | Nilsson et al. |
| 2002/0157124 | A1 | 10/2002 | Goldsmith et al. |
| 2003/0131364 | A1 | 7/2003 | Duff |
| 2003/0157519 | A1 | 8/2003 | Zhang et al. |
| 2004/0143860 | A1 | 7/2004 | St. George-Hyslop |
| 2005/0064390 | A1 | 3/2005 | Berger et al. |
| 2010/0162415 | A1 | 6/2010 | Ferrara |
| 2010/0279317 | A1* | 11/2010 | Smith ................. C07K 14/7051 435/7.21 |
| 2011/0195454 | A1* | 8/2011 | McWhirter et al. ......... 435/69.6 |

FOREIGN PATENT DOCUMENTS

| CN | 1656114 A | 8/2005 |
| CN | 101506235 A | 8/2009 |

OTHER PUBLICATIONS

Mehrota et al. (2009) J. Immunol., vol. 182 (Meeting Abstract Supplement), abstract 41.39.*
Wu et al. (2002) Nature, vol. 418, 552-556.*
Sullivan et al. (1997) J. Biol. Chem., vol. 272(29), 17972-17980.*
De Strooper (2003) Neuron, vol. 38, 9-12.*
Doyle et al. (2012) Transgenic. Res., vol. 21(2), 327-349.*
Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369.*
Prelle et al. (2002) Anat. Histol. Embryol., vol. 31, 169-186.*
Munoz et al. (2009) Stem Cell Rev. and Rep., vol. 5, 6-9.*
Allen et al., "Somatostatin receptor 2 knockout/lacZ knockin mice show impairedmotor coordination and reveal sites of somatostatin action within the striatum" Eur J Neurosci 17, 1881-1895 (2003).
Brian Sauer, "Site-specific recombination: developments and applications" Curr. Opin. Biotechnol., 5:521-527 (1994).
Cheung et al., "Humanized mouse lines and their application for prediction of human drug metabolism and toxicological risk assessment" J. Pharmacol. Exp. Ther. 327 (2): 288-299 (2008).
Ferrara et al., "Discovery and Development of Bevacizumab, an Anti-VEGF Antibody for Treating Cancer" Nat Rev. Drug. Discov. 3: 391-400 (2004).

(Continued)

Primary Examiner — Anne Marie S Wehbe
(74) Attorney, Agent, or Firm — Jun He Law Offices P.C.; James J. Zhu

(57) ABSTRACT

This present invention relates to transgenic animals useful to study human diseases. Specifically, the invention relates to transgenic animals expressing at least two human proteins (optionally in replacement of the counterpart proteins in the animal) whereas a first human protein interacts with a second human protein. The transgenic animals can then be used for evaluating drugs or building disease models that are related to the expressed human proteins in the animals. The animals and methods disclosed herein reduce the possibility identifying a false-positive compound—the compound that show an effect in a naturally-occurring, non-transgenic animal but may not necessarily work or be therapeutic in human, since the compound may only interrupt the interaction between two animal proteins not necessarily two related human proteins. Also, the animals and methods disclosed herein reduce the possibility of identifying a false-negative compound—a compound that does not work or have any effect in a naturally-occurring, non-transgenic animal but may have therapeutic effect in human, since the compound may only interrupt the interaction between at least two relevant human proteins not necessarily two related animal proteins.

6 Claims, No Drawings

(56) References Cited

OTHER PUBLICATIONS

Fuh et al., "Structure-Function Studies of Two Synthetic Anti-vascular Endothelial Growth Factor Fabs and Comparison with the Avastin™ Fab" J. Biol. Chem. 281: 6625-6631 (2006).
Gerber et al., "Mice expressing a humanized form of VEGF-A may provide insights into the safety and efficacy of anti-VEGF antibodies" PNAS 104 (9): 3478-3483 (2007).
Greaves et al., "First Dose of Potential New Medicines to Humans: How Animals Help" Nat. Rev. Drug Discov. 3: 226-236 (2004).
Makita et al., "Multiple renal cysts, urinary concentration defects, and pulmonary emphysematous changes in mice lacking TAZ" Am J Physiol Renal Physiol 294: F542-F553 (2008).
Malik et al., "Generation of knock-in mice expressing humanized forms of VEGF to study the pharmacological effects of Avastin during tumor angiogenesis" Cellular, Molecular, and Tumor Biology 95: Angiogenesis Mechanisms and Microenvironment (Abstract #4782, 2004).
Melanie A. Felmlee et al., "Cytochrome P450 Expression and Regulation in CYP3A4/CYP2D6 Double Transgenic Humanized Mice", Drug Metabolism and Disposition, 36 (2): 435-441 (2008).
Mihara et al., "Human CXCR2 (hCXCR2) takes over functionalities of its murine homolog in hCXCR2 knockin mice" Eur J Immunol 35: 2573-2582 (2005).
Muller et al., "VEGF and the Fab fragment of a humanized neutralizing antibody: crystal structure of the complex at 2.4 A resolution and mutational analysis of the interface" Structure 6: 1153-1167 (1998).
Olson et al., "Concordance of the toxicity of pharmaceuticals in humans and in animals" Regul. Toxicol. Pharmacol. 32: 56-67 (2000).
Roebroek et al., Transgenic Mouse Methods and Protocols, Hofker and van Deursen eds., Methods in Mol Biol, 693:257-275 (2011).
Sakurai et al., "Essential role of Flk-1 (VEGF receptor 2) tyrosine residue 1173 in vasculogenesis in mice" PNAS 102 (4): 1076-1081 (2005).
Willinger et al., "Human IL-3/GM-CSF knock-in mice support human alveolar macrophage development and human immune responses in the lung" PNAS 108 (6): 2390-2395 (2011).
Wirth et al., "Road to precision: recombinase-based targeting technologies for genome engineering" Curr. Opin. Biotechnol., 18: 411-419 (2007).
"International Search Report of PCT/US2011/062272".
Shikhar Mehrotra et al., "Development of a transgenic mouse with high affinity TCR reactive to human tyrosinase epitope" The Journal of Immunology, 2009, vol. 182, No. 41, pp. 39.

* cited by examiner

HUMANIZED TRANSGENIC ANIMAL

CROSS-REFERENCE TO RELATED APPLICATIONS

This application claims priority to U.S. Provisional Application Ser. No. 61/417,411, filed Nov. 27, 2010, which is specifically incorporated by reference in its entirety.

FIELD OF THE INVENTION

This present invention generally relates to transgenic animals useful to study human diseases. Specifically, the invention relates to transgenic animals expressing at least two human proteins whereas a first human protein dynamically interacts with a second human protein.

BACKGROUND OF THE INVENTION

Non-human animals used during the research and investigation of human diseases provide a useful means of better understanding the disease without the added risk of causing harm to an actual human being during the process. Many drugs, treatments and cures for human diseases have been developed by first being tested in animals (see, e.g., Greaves et al., 2004, Nat. Rev. Drug Discov. 3, 226-236; Olson et al., 2000, Regul. Toxicol. Pharmacol. 32, 56-67).

One of the drawbacks for using non-human animals in research of human diseases and preclinical trials is that a drug showing efficacy when applied to animals may not be effective in human due to the difference between target human protein and animal protein. Such disparity of drug efficacy may result in expensive pre-clinical and clinical failure. On the other hand, human-animal protein difference may lead to a miss of candidates effective in treating human diseases when animal model is used to screen or test drugs. For example, Avastin, a neutralizing antibody of human Vascular Endothelial Growth Factor (VEGF) and a drug inhibiting human cancer angiogenesis, interacts poorly with murine VEGF, while it blocks human VEGF's binding to human VEGF receptor (Ferrara et al., 2004, Nat Rev Drug Discov. 3, 391-400). This dramatic disparity is resulted from a single amino acid difference between the human epitope that Avastin binds to and the corresponding murine epitope (Fuh et al., 2006, J Biol Chem 281: 6625-31; Muller et al., 1998, Structure 6: 1153-67). It has been reported that 19 amino acid residues of VEGF participate in the interface of the complex of human VEGF and its neutralizing antibody (Muller et al., 1998, Structure 6: 1153-67). Comparison of human and mouse VEGF sequence shows that among the 19 amino acid residues only one residue (Gly88) in human VEGF differs from its counterpart in mouse (see Muller et al., 1998, Structure 6: 1153-67).

Therefore, in order to search and evaluate drug candidates in treating a human disease, there are needs to develop animal models in which a human gene is introduced to express a human protein in the animal cells and to mimic the human disease. Furthermore, in order to prevent the interaction between the drug candidates and the human protein being interfered by the endogenous animal proteins, there are needs to have endogenous animal gene corresponding to the desired human gene being damaged, such that the introduced human gene operably replaces the corresponding animal gene. Some transgenic animals in which one human gene replaces a corresponding animal gene have been made to meet the needs. For example, transgenic mice in which human VEGF gene replaces endogenous mouse VEGF gene has been made to study the role of human VEGF in normal and pathological angiogenesis (US Pat Pub No. 2010/0162415 A1).

However, transgenic mice expressing only one human gene have limitations in searching and evaluating drug candidates in treating human diseases because, to exert their effects on the human diseases, the drug candidates often need to act in a desired way on a targeted protein-protein interaction that underlies the physiological process of the human diseases. For example, a neutralizing antibody of human VEGF inhibits angiogenesis by blocking human VEGF's binding to human VEGF receptor. A neutralizing antibody candidate may not show any effect on transgenic mice expressing only human VEGF as the expressed human VEGF may not interact in the same manner with murine VEGF receptor as with human VEGF receptor. Therefore, there are needs to develop animal models expressing both human proteins involved in the targeted protein-protein interaction that underlies the physiological process of the human diseases.

This disclosure provides a transgenic animal expressing at lease two human proteins whereas a first human protein dynamically interacts with a second human protein, whereas the consequence of the interaction between the first human protein and the second human protein forms a part of a cascade of signaling pathway that direct cellular changes. In some preferred embodiments, when the second human protein interacts with a third human protein in the cascade of signaling pathway, the third human protein is also introduced into the transgenic animal. More preferably, when the third human protein interacts with a fourth human protein in the cascade of signaling pathway, the fourth human protein is also introduced into the transgenic animal, and so forth, until the whole cascade of signaling pathway is completely introduced into the transgenic animal.

SUMMARY OF THE INVENTION

The present disclosure generally relates to non-naturally occurring non-human transgenic animals expressing at least two human genes whereas a first human protein expressed from a first human gene interacts with a second human protein expressed from a second human gene.

The protein-protein interaction of the current disclosure includes any dynamic association between a first protein and a second protein, whereas the consequence of the protein-protein interaction forms a part of a cascade of signaling pathway that directs cellular changes. In one aspect, the protein-protein interaction includes a ligand binding to a cell-surface receptor in transducing signals from the exterior of a cell. In another aspect, the protein-protein interaction includes a first protein with enzymatic activity binding to its substrate to modify it. In yet another aspect, the protein-protein interaction includes a first protein acting as a scaffold that binds all or some of the proteins in a cascade of signaling pathway to form a complex.

In certain embodiments, when the genome of the targeted animal comprises an endogenous gene homologous to the desired human gene, the expression of endogenous animal gene is silenced such that the endogenous animal gene is operably replaced by the desired human gene in the humanized transgenic animals. In some preferred embodiments, the desired human gene is inserted in the locus of the corresponding animal gene, and more preferably, under the control of the regulatory sequences of the corresponding animal gene.

In one aspect, the humanized transgenic animals disclosed in the present invention provide a system to understand how human proteins interact with each other. In certain embodiments, the humanized transgenic animals provide a method to identify molecules that modulate the interaction between the desired human proteins. The method comprises administrating said molecules to the humanized transgenic animal, and monitoring the modulation of interactions between the desired human proteins.

In another aspect, the humanized transgenic animals provide a model of a human disease associated with the desired human genes.

In yet another aspect, the humanized transgenic animals provide a method to identify novel therapeutic agents for a human disease associated with the desired human genes. The method comprises: a) administrating the agent to the humanized transgenic animal, wherein the animal mimics a human disease associated with the desired human genes; and b) monitoring the effectiveness of the agents on the human disease in the humanized transgenic animal.

DETAILED DESCRIPTION

Protein-Protein Interaction

For describing the relationship of desired human proteins, the interactions of proteins include any direct-contact association of protein molecules. Protein-protein interaction includes permanent association of protein molecules to form a protein complex that functions as a protein machine. For example, two heavy chains interact with two light chains to form an immunoglobulin for recognizing antigens. For another example, an alpha-subunit interacts with a beta-subunit to form a T-cell receptor for recognizing antigens bound to major histocompatibility complex (MHC). Additional examples of protein complex include hemoglobin which consists of two alpha-globin proteins and two beta-globin proteins.

In a preferred aspect of the present invention, protein-protein interaction occurs when a first protein associates transiently with a second protein, whereas the consequence of the dynamic protein-protein interaction forms a part of a cascade of signaling pathway that directs cellular changes. In some embodiments, dynamic protein-protein interaction includes a protein ligand binding to a cell-surface receptor in transducing signals from the exterior of a cell. For example, the binding of VEGF to VEGF receptor (VEGFR) leads to a cascade of different signaling pathways, including intracellular activation of the mitogen-activated protein kinase (MAPK) pathway and the phosphatidylinositol 3'-kinase (PI3K) pathway, resulting in the up-regulation of genes involved in mediating the proliferation and migration of endothelial cells and promoting their survival and vascular permeability (Holmes et al. (2007) Cellular Signaling 19, 2003-12).

In other embodiments, dynamic protein-protein interaction includes a first protein with enzymatic activity (e.g., protein kinase) binding to its substrate to modify it (e.g., add phosphate). The modification of protein includes, without intent of limitation, phosphorylation, de-phosphorylation, hydroxylation, acetylation, ubiquitination and proteolytic cleavage. For example, upon receiving extracellular stimuli (e.g., mitogens, osmotic stress, heat shock and proinflammatory cytokines), activated mitogen-activated protein (MAP)-kinase-kinase interacts with its substrate MAP-kinase, leading to the phosphorylation of both a threonine and a tyrosine on MAP-kinase. The phosphorylated MAP-kinase relays the signal downstream by phosphorylating various proteins in the cells, regulating diverse cellular activities, such as gene expression, mitosis, proliferation, differentiation, and cell apoptosis. For another example, dynamic protein-protein interaction occurs when protein phosphatases bind to phosphorylated MAP-kinases and remove phosphate from the tyrosine or the threonine, ensuring that MAP-kinases are activated only transiently in response to extracellular signals. For yet another example, under physiological oxygen condition, hypoxia-inducible-factor (HIF) prolyl-hydroxylases interact with alpha subunits of HIF and hydroxylate the conserved proline residues. The modified HIF alpha subunits then interact with and are ubiquitinated by VHL E3 ubiquitin ligase, which labels the HIF alpha subunits for rapid degradation by the proteasome. In hypoxia conditions, HIF prolyl-hydroxylases are inhibited, since they utilize oxygen as a co-substrate, leading to the stabilization of HIF. The stabilized HIF then transcriptionally regulates an array of genes to promote survival in hypoxia conditions. For yet another example, upon receiving intracellular or extracellular pro-apoptotic signal, initiator cysteine-dependent aspartate-specific proteases (caspases), e.g., caspases 8, 10, 9, 2, interact with effector caspases, e.g., caspases 3, 7, 6, and activate the effector caspases through proteolytic cleavage. The active effector caspases then proteolytically degrade an array of intracellular proteins to carry out the cell death program.

The protein-protein interaction can be identified in various ways that are within the skill in the art (see, general, Protein-Protein Interactions: A Molecular Cloning Manual, 2nd ed., Golemis and Adams, ed., Cold Spring Harbor Laboratory Press (2005)). For instance, protein-protein interactions can be identified using molecular and biochemical methods such as conventional column chromatography, co-immunoprecipitation, pull-down assay, yeast two-hybrid, and phage display. Alternatively, the interaction of proteins can be identified using biophysical methods such as Fluorescence resonance energy transfer (FRET), mass spectrometry and Surface Plasmon Resonance (SPR). Those skilled in art can also identify the interaction of proteins by referring to the publicly available database such as BioGRID, STRING, MIPS (mammalian protein-protein interaction database) and DIP (Database of Interacting Proteins).

The human protein herein includes both fully human protein or humanized protein (e.g., like humanized antibodies) wherein the functional portion of the protein is originated from human protein and the framework is originated from an animal protein.

Protein-Protein Interaction and Human Diseases

As protein-protein interactions form a part of a cascade of signaling pathway that directs cellular changes, abnormal protein-protein interactions perturb the normal consequence in the cell and contribute to human diseases. For example, the interaction of VEGF and VEGFR, which induces vascular endothelial cells proliferation, pruning and reorganization to form new blood vessels from the preexisting vascular network, is pivotal for abnormal angiogenesis in the development of many human diseases (Ferrara and Davis-Smyth, Endocrine Rev. 18:4-25 (1997); Ferrara, J. Mol. Med. 77:527-543 (1999). The VEGF is overexpressed by the majority of human tumors examined (Berkman et al., J Clin Invest 91:153-159 (1993); Brown et al., Human Pathol. 26:86-91(1995); Brown et al., Cancer Res. 53:4727-4735(1993); Mattern et al., Brit. J. Cancer. 73:931-934 (1996); and Dvorak et al., Am J. Pathol. 1461029-1039 (1995)). Hyperactive VEGF-VEGFR interaction, resulting from VEGF over-expression, has been implicated with poor prognosis in breast cancer. In addition, aberrant VEGF- VEGFR interaction in eye fluids is highly correlated to the presence of active proliferation of blood vessels in patients with diabetic and other ischemia-related retinopathies (Aiello et al., New Engl J. Med. 331:1480-1487 (1994)).

For another example, the interaction between MAP kinase kinase (MAPKK) and MAP kinase (MAPK), which results in the phosphorylation and activation of MAPK, plays a pivotal role in the mitogenic signal transduction pathway (Raman Metal., Oncogene 26(22):3100-12 (2007)). The mitogenic signal transduction pathway is involved in the cellular response to many stimuli such as cytokines, growth factors, antigens, toxins, and stresses such as temperature change and irradiation, and changes in cell shape, cell-cell interaction and extracellular matrix composition. Accordingly, aberrant activation of MAPK appears to contribute to many human diseases, such as cancer, inflammation and neuro-degeneration (Cuendaa and Rousseaua, Biochim Biophys Acta. 1773(8):1358-75 (2007); Dhillon et al., Oncogene 26(22):3279-90 (2007)).

For yet another sample, the interaction between amyloid precursor protein (APP), an integral membrane protein, and gamma-secretase results in the cleavage of APP, producing a short 39-42 amino acid peptide called amyloid beta. Over-production and aggregate of amyloid beta forms abnormally folded amyloid fibril, the primary component of amyloid plaques found in the brains of Alzheimer's disease patients. Accumulation of amyloid fribril induces programmed cell death and is believed to give rise to the pathology of Alzheimer's disease (Van Broeck et al., Neurodegener Dis 4(5): 349-65 (2007)).

Humanized Transgenic Animals

The present disclosure provides a transgenic animal wherein at least two human genes encoding at least two human proteins are expressed in the targeted animal. The term "transgenic animal" is intended to include any non-naturally occurring non-human animal in which one or more of the cells of the animal contain nuclei acid encoding a human gene, which has been introduced by way of human intervention, such as by transgenic techniques well known in the art. See supra for detail. The term "non-human animal" means an animal excluding human, and is intended to include any vertebrate such as mammals, birds, reptiles, amphibians and fish. Suitable mammals include rodents, non-human primates, sheep, dogs and cattle. Preferred non-human animals are selected from the rodent family including rat and mouse, most preferably mouse. The term "naturally-occurring" as used herein as applied to an object means that an object can be found in nature.

In particular, the present disclosure provides a transgenic animal wherein the desired human proteins expressed in the targeted animal interact with each other. For example, a humanized transgenic animal described in this disclosure could be a transgenic mouse expressing both human VEGF and human VEGFR. For another example, a humanized transgenic animal described in this disclosure could be a transgenic mouse expressing both human MAPKK and human MAPK. For yet another example, a humanized transgenic animal described in this disclosure could be a transgenic mouse expressing both human APP and human gamma-secretase.

The humanized transgenic animals described in this disclosure are intended to include transgenic animals expressing more than two human proteins whose interaction form a part of a cascade of signaling pathway, i.e. a first human protein interact with a second human protein, which subsequently interacts with a third human protein. For example, a humanized transgenic animal may be a transgenic mouse expressing human MAP3K, human MAP2K and human MAPK. In some embodiments, the third human protein may subsequently interact with a fourth human protein, which may subsequently interact with a fifth human protein, and so on, until all the human proteins that form the whole cascade of signaling pathway are introduced into the transgenic animal. For example, a humanized transgenic animal may be a transgenic mouse expressing human VEGF, human VEGFR, human GRB2, human SOS, human MAP3K, human MAP2K and human MAPK.

In some preferred embodiments, the endogenous animal gene substantially homologous to the desired human gene in the transgenic animal genome is disrupted such that the desired human gene operably replaces the endogenous animal gene.

Corresponding Animal Gene

In some preferred embodiments, the animal genes corresponding to the transferred human genes are silenced such that the transferred human genes operably replace the endogenous animal genes. The term "corresponding" or "substantially homologous," when describing the relationship of an animal gene to a human gene, are used interchangeably, and mean that the nucleotide sequences of two genes, when optimally aligned and compared with appropriate nucleotide insertions or deletions have at least about 80% sequence identity, more preferably about 85% sequence identity, more preferably about 90% sequence identity, more preferably about 95% sequence identity, and more preferably about 99% sequence identity to another. Methods of aligning two sequences and identifying percent identity are known to those of skill in art. Alignment for purposes of determining percent nucleotide sequence identity can be performed in various ways that are within the skill in the art, for example, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequence being compared.

A gene is "silenced" when the expression of the normal protein product from the gene is inhibited. A gene is often silenced by disrupting the genomic sequence of the gene. A gene is disrupted when a fragment of DNA locates and recombines with an endogenous homologous sequence. The disruptions may include insertion, missense, frameshift, deletion, or substitutions, or replacements of DNA sequences, or any combination thereof. Insertions include the insertion of entire genes. when Disruption can alter the normal gene product by inhibiting its production partially or completely. In a preferred embodiment, the disruption is a null disruption so that the gene has no significant expression.

The term "operably replace" or "replacement" as used herein mean that in the transgenic animal wherein the desired human gene is introduced, the endogenous animal gene corresponding to the introduced human gene is silenced, such that the introduced human gene functionally substitutes the corresponding animal gene. For example, in a humanized transgenic mouse whereas both human VEGF and human VEGFR are introduced, the endogenous murine VEGF and VEGFR are further silenced such that the introduced human VEGF anf VEGFR protein functionally substitute the murine VEGF and VEGFR.

In some more preferred embodiments, the desired human gene is inserted in the same loci as the corresponding endogenous animal gene such that the expression of the desired human gene is controlled by the transcriptional regulatory sequence of the corresponding endogenous animal gene. The term "transcriptional regulatory sequence" indicates to nucleotide sequences having function to regulate or control transcription of protein coding sequences with which they are operably linked. Examples of such a transcriptional regulatory sequence include, but are not limited to, a promoter, an enhancer, a silencer and an initiation signal. In a preferred embodiment, a humanized transgenic mouse containing both human VEGF and VEGFR gene can be made so that the protein coding sequence of the human VEGF gene is inserted in the loci of the endogenous murine VEGF gene. The insertion can be made through recombination such that the introduced protein coding sequence of the human VEGF gene substitutes the corresponding protein coding sequence of the murine VEGF gene. This allows the expression of the introduced human VEGF gene to be controlled by the transcriptional regulatory sequence of the murine VEGF gene.

Production of Humanized Transgenic Animals

Methods for generating transgenic animals of the present invention, including knock-outs and knock-ins, are well known in the art (see, generally, Gene Targeting: A Practical Approach, Joyner, ed., Oxford University Press, Inc. (2000); Transgenesis Techniques: Principles and Protocols, Clarke, ed., Human Press (2002)). In the present disclosure, generation of the humanized transgenic animal involves introduction of desired human genes into the genome of a host animal. In some embodiments, the endogenous loci of the animal gene corresponding to the desired human gene may be disrupted. Generation of the humanized transgenic animal may also involve a replacement of the endogenous animal gene with the corresponding human gene, wherein the desired human gene is introduced at the same location as the corresponding endogenous animal gene.

Introducing Human Genes into Non-Human Animals (i) Introducing Human Genes into Animals by Using Embryonic Stem (ES) Cell The basic approach towards production of the humanized transgenic animals is to introduce the desired human genes into the targeted non-human animals. In the present disclosure, the humanized transgenic animals are preferably produced from an embryonic stem (ES) cell having the desired human genes inserted in the genome. The desired human genes can be efficiently introduced into the ES cells by DNA transfection or by retrovirus-mediated transduction (see, e.g., Lakshmipathy et al., Stem Cells, 22(4):531-43 (2004); Bowen, Retroviral Infection, in Transgensis Techniques: Principles and Protocols, Clarke eds., Human Press, pp 83-90 (2002)). The transformed ES cells can then be combined with blastocysts from a non-human animal. The ES cells thereafter colonized the embryo and contribute to the germ line of the resulting chimeric animal (see, e.g., Wells, Production of chimeras derived from murine embryonic stem cells, in Transgensis Techniques: Principles and Protocols, Clarke eds., Human Press, 127-149 (2002)).

In order to introduce a desired human gene of into ES cells, a polynucleotide molecule comprising the desired human gene is inserted into a vector, preferably a DNA vector, to generate a transgene construct (see, general, Molecular Cloning A Laboratory Manual, 2nd ed., Sambrook, Fritsch and Maniatis eds., Cold Spring Harbor Laboratory Press, 1989) The term "construct" refers to a polynucleotide molecule that comprises a gene or a nucleic acid sequence of particular interest. Typically, the construct also includes a selectable marker gene and appropriate control sequences. A "transgene construct" refers to a construct in which the gene of interest is a desired human gene. A "targeting construct" refers to a construct in which the nuclei acid sequence of interest is a sequence that is substantially homologous to an endogenous sequence in a target animal and that provides for integration of the construct into the genome of the targeted animal.

A "selectable marker" means an identifying factor, usually an antibiotic or chemical resistance gene, that is able to be selected for based upon the marker gene's effect, i.e., resistance to an antibiotic, enzymes, fluorescent markers, and the like, wherein the effect is used to track the inheritance of a nuclei acid of interest and/or to identify a cell or organism that has inherited the nucleic acid of interest. Examples of selectable marker genes known and used in the art include: genes providing resistance to ampicillin, streptomycin, gentamycin, kanamycin, hygramycin, neomycin, and the like.

It will be understood that separate constructs containing a first human gene and a second human gene, respectively, may be generated, or a single construct may contain a plurality of the desired human genes.

The polynucleotide molecule preferably further comprises regulatory sequences functionally linked to the desired human gene. A "regulatory sequence" means a nucleic acid sequence that regulates the expression of a second nucleic acid sequence. The regulatory sequences may comprise the nucleic acid sequences upstream (5') or downstream (3') from the second nucleic acid sequence. Those nearby sequences often impact processing and/or expression of the second nucleic acid sequence in a desired cell type. For example, the regulatory sequences may include sequences, such as promoters, enhancers, terminators, and the like, that provide for the expression of a coding sequence in a host cell. For another example, the regulatory sequences may also include a 3' untranslated region downstream of the coding sequence of a desired human gene. Such regions can stabilize the RNA transcript of the desired human gene and thus increase the yield of the desired human protein. The 3' untranslated regions include sequences that provide a polyA signal. Such sequences may be obtained, for example, from the SV40 small t antigen, the endogenous 3' untranslated region of the desired human gene, or other 3' untranslated sequences known in the art.

Preferably, the regulatory sequences are of human genomic origin, and include one or more introns. For example, the polynucleotide molecule can include regulatory sequences located in the 5'-flanking region of the desired human gene, operably linked to the coding sequences in a manner capable of replicating and expressing the desired human gene in a host cell. For another example, the regulatory sequences comprise the endogenous promoter sequences naturally associated with the desired human gene. For yet another example, the promoter provides for tissue specific expression at a level similar to that level of expression in human.

Alternatively, said regulatory sequences can be those regulatory sequences associated with the corresponding endogenous gene in the host non-human animal. For example, the murine regulatory sequences, such as a promoter, for the murine gene corresponding to the desired human gene can be included in the polynucleotide molecule and functionally linked to the coding sequences of the desired human gene such that the desired human gene can be properly expressed in the mouse cells.

The polynucleotide molecule comprising the desired human gene can be prepared using methods well known in the art. For example, the polynucleotide molecule can be prepared as part of a larger plasmid. Such preparation allows the cloning and isolation of the correct constructs in an efficient manner as is known in the art. The various methods employed in the preparation of the plasmids and transformation of host organisms are known in the art (see, e.g., Molecular Cloning A Laboratory Manual, 2nd ed., Sambrook et al. eds., Cold Spring Harbor Laboratory Press, 1989). In addition, a yeast artificial chromosome (YAC) may be employed to isolate, clone and transfer the whole locus of the desired human gene. Alternatively, a bacterial artificial chromosome (BAC) library (see, e.g., Genomic BAC libraries from Invitrogen, Carlsbad Calif.) can provide nucleic acid sequences for the desired human genes as well as regulatory sequences.

The prepared transgene construct may be introduced into ES cells using any method known in the art. Various techniques for transforming mammalian cells may be employed in the present invention, including, for example: microinjection, retrovirus mediated gene transfer, electroporation, transfection, or the like (see, e.g., Gordon, Intl. Rev Cytol., 115:171 (1989); Keown et al., Methods in Enzymology, 185:527-537 (1990); Mansour et al., Nature, 336:348-352 (1988)).

ES cells are typically obtained from pre-implantation embryos cultured in vitro (see, e.g., Evans, M. J. et. al., Nature 292: 154-156 (1981); Bradley, M. O. et al., Nature 309:255-258 (1984); Gossleer et al., Proc. Natl. Acad. Sci. USA 83:9065-9069 (1986); and Robertson et al., Nature 322:445-448(1986)). The ES cells are cultured and prepared for introduction of the transgene construct using methods well known in the art (see, e.g., Teratocarcinomas and Embryonic Stem cells: a Practical Approach, Robertson eds., IRL Press (1987); Bradley et al., Current Topics in Devel. Biol. 20:357-371 (1986); Hogan et al., Manipulating the Mouse Embryo: A Laboratory Manual, Cold Spring Harbor Laboratory Press (1986); Thomas et al., Cell 51:503 (1987); Koller et al., Proc. Natl. Acad. Sci. USA, 88:10730 (1991); Dorin et al., Transgenic Res. 1:101 (1992); and Veis et al., Cell 75:229 (1993)). The ES cells that will be inserted with the desired human genes are derived from an embryo or blastocyst of the same species as the developing embryo into which they are to be introduced. ES cells are typically selected for their ability to integrate into the inner cell mass and contribute to the germ line of an individual when introduced into the host animals in an embryo at the blastocyst stage of development. Thus, any ES cell line having this capacity is suitable for use in the practice in the present invention.

After the transgene construct has been introduced into ES cells, the cells in which successful gene insertion has occurred are identified. Insertion of the transgene construct into the genome of host cells is typically detected by identifying cells for expression of a selectable marker gene. For example, the cells transformed with the transgene construct are subjected to treatment with an appropriate drug (e.g., G418) that selects against cells not expressing the selectable marker gene (e.g., neomycin resistance gene). Only those cells expressing the selectable marker gene (e.g., neomycin resistance gene) survive and grow under certain conditions.

Selected ES cells are then injected into an embryo (a blastocyst or other stage of development suitable for the purposes of creating a viable animal) of an animal to create chimeras (see, e.g., Bradley, A. Teratocarcinomas and Embryonic Stem Cells: A Practical Approach, E. J. Robertson, ed., IRL, Oxford, pp 113-152 (1987)). Alternatively, selected cells can aggregate with dissociated embryo cells to form the aggregate chimera. A chimeric embryo can then be implanted into a suitable pseudo-pregnant female foster animal and the embryo brought to term. Chimeric progeny harboring the desired human gene in their germ cells can be used to breed animals in which all cells of the animal contain the desired human gene (see, e.g., id.).

(ii) Introducing Human Genes into Animals by Using Site-Specific Recombination System An additionally preferred method for introducing desired human genes into animals includes employment of site-specific recombination system (see, general, Roebroek et at., Trangenic Mouse Methods and Protocols, Hofker and van Deursen eds., Methods in Mol Biol, 693:257-275 (2011)) This method allows the desired human gene to be integrated in a pre-determined position in the genome of the host animals (see, e.g., U.S. Pat. Nos. 7,846,732; 7,972,857). Many site-specific recombination systems (e.g., Cre/Lox P system, ΦC31-derived integrase system) are developed from some bacteriophage and integrative plasmids which utilize the system to stably integrate their genome into those of their hosts and excise the genome from the host genome. In these systems, the minimal requirements for the recombination reaction are a recombinase enzyme, which catalyzes the recombination event, and two recombinase recognition sequences (Sadowski, J. Bacteriol. 165: 341-347 (1986); Sadowski, FASEB J. 7: 760-767 (1993)). For phage integration systems, the recombinase recognition sequences are referred to as attachment (att) sites, with an attP element from phage DNA and the attB element present in the bacterial genome. The recombinase enzyme binds to both attachment sites and catalyzes a conservative and reciprocal exchange of DNA strands that result in integration of the circular phage or plasmid DNA into host DNA.

In some embodiments of the present invention, a first recombinase recognition sequence (e.g., attB) for a site-specific recombinase (e.g., ΦC31 integrase) is inserted at a genomic site, either at a random or at a pre-determined location, in appropriate animal cells (e.g., ES cells). Subsequently, the animal cells are transfected with a transgene construct carrying the desired human gene and a second recombinase recognition sequence (e.g., attP). A source for the recombinase (plasmid, RNA, protein, or virus-expressing recombinase, e.g., ΦC31 integrase) is also provided to the transfected animal cells. Recombination between the first and second recombinase recognition sequence leads to integration of the desired human gene in the genome of the animal cells. The animal cells with successful integration events are then selected and used to develop into humanized transgenic animals using the methods described in the previous sections.

(iii) Introducing Human Genes into Animals by Using Embryos

In addition to the above described methods for introducing desired human genes into non-human animals using ES cells, the humanized transgenic animals of the invention can also be produced by introducing desired human genes into embryos at various developmental stages. Different methods are used depending on the stage of development of the embryo. The specific line(s) of any animal used to practice this invention are selected for general good health, good embryo yields, good pronuclear visibility in the embryo, and good reproductive fitness. The line(s) used to practice this invention may themselves be transgenic, and/or may be knockouts. Preferably the same line will be used for preparation of both the initial knockout animals and the transgenic animals. This will make subsequent breeding and the crossing more efficient.

Any means known in the art can be used to introduce the desired human gene into the embryo. For example, the desired human gene can be introduced into an animal by microinjection of the transgene construct into the pronuclei of the fertilized mammalian egg(s) to cause one or more copies of the transgene construct to be retained in the cells of the developing animals. The eggs thereafter may be incubated in vitro for varying amount of time, or reimplanted into the surrogate host, or both. One common method is to incubate the embryos in vitro for about 1-7 days, depending on the species, and then reimplant them into surrogate host.

Retroviral infection can also be used to introduce desired human genes into the embryo. The developing non-human embryo can be cultured in vitro to form blastocyst to be used as targets for retroviral infection (Jaenich, R. Proc. Natl. Acad. Sci. USA 73:1260-1264 (1976)). The blastomeres are usually enzymatically treated to remove the zona pellucida in order to achieve efficient infection (Manipulating the Mouse Embryo, Hogan eds., Cold Spring Harbor Laboratory Press (1986)). The viral vector system used to introduce the desired human gene is typically a replication-defective retrovirus carrying the desired human gene (Jahner et al., PNAS 82:6927-6931 (1985); Van der Putten et al., PNAS 82:6148-6152 (1985)). Infection is easily and efficiently obtained by culturing the blastomeres on a monolayer of virus-producing cells (Van der Putten, supra; Stewart et al., EMBO J. 6:383-388 (1987)). Alternatively, infection can be performed at a later stage by injecting virus or virus-producing cells into the blastocoele (Jahner et al., Nature 298:623-628 (1982)). In addition, it is also possible to introduce transgenes into the germ line by intrauterine retroviral infection of the midgestation embryo (Jahner et al., Nature 298:623-628 (1982)). Most of the founders will be mosaic for the transgene since incorporation occurs only in a subset of the cells which formed the transgenic animal. Further, the founder may contain various retroviral insertions of the transgene at different positions in the genome which generally will segregate in the offspring.

Replacing Endogenous Animal Genes with Corresponding Human Genes

In some preferred embodiments of the present invention, the endogenous loci of the animal gene corresponding to the desired human gene are silenced to inhibit the expression of the endogenous animal gene, such that the introduced human gene operably replaces the endogenous animal gene. In more preferred embodiments, the introduced human gene completely replaces the protein coding sequences of the endogenous animal gene. More preferably, the introduced human gene is operably linked, as a consequence of homologous integration, to the transcriptional regulatory sequences (e.g., an enhancer or a promoter) of the endogenous animal gene, so that the desired human gene is expressed under the control of the transcriptional regulatory sequences from the correspondingly endogenous animal gene locus.

(i) Inactivation of Endogenous Loci through Homologous Recombination

Inactivation of the endogenous loci is preferably achieved by targeted disruption through homologous recombination in appropriate animal cells (see, generally, Gene Targeting: A Practical Approach, Joyner, ed., Oxford University Press, Inc. (2000)). Preferred cell types used in the present invention include embryonic stem cells. Methods for manipulating ES cells are described in the previous sections and the reference thereof.

A targeting construct that comprises a nucleotide sequence that is substantially homologous to an endogenous sequence of a targeted animal gene need to be prepared in order to facilitate homologous recombination. The targeting construct is so produced that after homologous recombination the expression of the targeted animal gene is disrupted (e.g., the locus of the targeted animal gene is altered through insertion or deletion). The targeting construct may be produced using methods well known in the art (see, e.g., Molecular Cloning: A laboratory Manual, 2nd ed, Sambrook et al. eds., Cold Spring Harbor Laboratory Press (1989); DNA Cloning: A Practical Approach, Volumes I and II, Glover eds. (1985)). For example, the targeting construct may be prepared with standard methods, where sequences may be chemically synthesized, isolated from natural sources using PCR amplification, cloned from a vector harboring a sequence of interest (e.g., plasmids, phagemids, YACs, cosmids, BACs, bacteriophage DNA, other viral DNA), ligated, subjected to in vitro mutagenesis, or the like. The joined sequences may be analyzed by restriction analysis, sequencing, or the like.

Once an appropriate targeting constructs has been prepared, the targeting construct may be introduced into an appropriate animal cell using any method known in the art, including methods described in the previous sections (e.g., microinjection, retrovirus mediated gene transfer, electroporation, transfection).

After the targeting construct has been introduced into the animal cells, the successful homologous recombination events are identified using methods known in the art (see, e.g., Transgensis Techniques: Principles and Protocols, Clarke eds., Human Press, pp 83-90 (2002)). Typically, insertion of the targeting construct into the targeted gene is detected by identifying cells for expression of a selectable marker gene. For example, a positive-negative selection technique may be used to select homologous recombinants. In this process, a targeting construct carrying two selectable markers is employed. The cells transformed with the targeting construct are treated with a first selecting agent (e.g., a neomycin-like drug) to select for those cells expressing the positive selectable marker (e.g., a neomycin resistant gene), i.e. positive selection. Only those cells with introduction of the targeting construct and expressing the selectable marker gene survive and grow. A second selecting agent, such as gancyclovir (GANC) or FIAU (1-(2-deoxy 2-fluoro-B-D-arabinofluranosly)-5-iodouracil), is subsequently added to kill cells that express the negative selection marker, i.e. negative selection. Cells with non-homologous insertion that contain and express the negative selection marker (e.g., SV thymidine kinase) are killed by the second selecting agent, whereas cells with homologous recombination that do not contain and express the negative selection marker survive (see, e.g., Mansour et al., Nature 336:348-352, (1988); Capecchi, Science 244:1288-1292, (1989)).

The selected cells may be analyzed to confirm successful homologous recombination. Various techniques known in the art, such as PCR and Southern blot analysis, may be used to confirm homologous recombination events.

The selected cells are then injected into an embryo of an animal to create chimeras using the methods known in the art (see supra). Chimeric progeny harboring the homologous recombined DNA in their germ cells can be used to breed animals in which all cells of the animal contain the homologous recombined DNA.

After the animals containing the homologous recombined DNA are produced, the disruption of the expression of the targeted animal gene in the desired cell, tissue or animal may be screened by any suitable method. Standard methods to detect the disruption of the expression of the targeted animal gene include Western blot analysis using an antibody against the targeted animal protein. Additional methods for evaluating the disruption of the expression of the targeted animal protein include, without limitation, suitable biochemical assays such as histological stains for particular marker or enzyme activities, flow cytometric analysis, enzyme and/or immunological assays, and the like.

The transgenic animals wherein the targeted animal gene is disrupted are subsequently crossed to the transgenic animal harboring the corresponding human gene to breed the humanized transgenic animal wherein the endogenous animal gene is replaced by the corresponding human gene (see infra for details of crossing of transgenic animals).

(ii) Inactivation of Endogenous Loci by Using Site-Specific Recombination System An additionally preferred method for functional inactivation of endogenous loci includes employment of site-specific recombination system (e.g., Cre/LoxP system, Flp/FRT system, or ΦC31-derived integrase system; see supra for general description). As the starting point of this strategy, a first recombinase recognition sequence (e.g., attB) and a second recombinase recognition sequence (e.g., attP) is introduced into the animal genome, often through homologous recombination, such that a nucleic acid segment of a targeted animal gene is flanked by the two recombinase recognition sequences. Recombination between the two recognition sequences due to the introduction of a recombinase (e.g., ΦC31 integrase) leads to deletion of the nucleic acid segment and inactivation of the targeted animal gene (see Curr. Opin. Biotechnol., 18, 411-419 (2007)). In certain embodiments, the first recombination site and the second recombination site bears the same nucleic acid sequence (e.g., Lox P site) (see Curr. Opin. Biotechnol., 5:521-527 (1994)). The recombinase can be introduced through transfecting the animal cells by recombinase protein, or by a recombinase— expressing plasmid, RNA or virus. Alternatively, the recombinase can be expressed from a recombinase gene integrated in the genome of the animal cells under the control of a constitutive or inducible promoter.

(iii) Replacing Endogenous Animal Gene through Homologous Recombination

Preferably, replacing endogenous animal gene with corresponding human gene can be achieved through homologous recombination (see, e.g., Allen et al., Eur J Neurosci 17, 1881-1895 (2003); Makita et al., Am J Physiol Renal Physiol 294, F542-F553 (2008)). A replacement-type targeting construct is generally employed for homologous gene replacement. To make a replacement-type targeting construct, a nucleic acid sequence of a desired human gene is flanked between two homologous recombination sequences derived from the sequences of the animal genome. Double crossover between the homologous recombination sequences of the targeting construct and sequences of the animal genome results in targeted integration of the nucleic acid sequence of the desired human gene to the locus of the corresponding animal gene in the animal cells. Usually, the homologous recombination sequences of the targeting construct comprise sequences which flank the endogenous animal gene segments, so that homologous recombination results in concomitant deletion of the endogenous animal gene segments and homologous integration of the desired human gene segments (see Roebroek et at., Trangenic Mouse Methods and Protocols, Hofker and van Deursen eds., Methods in Mol Biol, 693:257-275 (2011)). An entire endogenous animal gene may be replaced with a desired human gene by a single targeting event or by multiple targeting events which sequentially replace individual exons. One or more selectable markers (e.g., positive or negative selectable marker gene), may be employed in the targeting construct. It is usually preferred that selectable markers are located in the intron regions of the desired human gene.

In some embodiments, replacing endogenous animal gene with the corresponding human gene can be achieved by using site-specific recombination system (e.g., Cre/LoxP system, Flp/FRT system, or ΦC31-derived integrase system; see, general, Roebroek et at., Trangenic Mouse Methods and Protocols, Hofker and van Deursen eds., Methods in Mol Biol, 693:257-275 (2011)). As the starting point of this strategy, two recombinase recognition sequences (e.g., LoxP, FRT, or attB/attP sequences) is introduced in appropriate animal cells (e.g., ES cells) by a first homologous recombination event, such that the two introduced recombinase recognition sequences flank the endogenous animal gene. A selectable marker gene (e.g., HygTK) is usually introduced in the animal cell in the first homologous recombination event, allowing positive selection (e.g., by hygromycin B) and negative selection (e.g., by ganciclovir). A transgene construct carrying the desired human gene corresponding to the endogenous animal gene is prepared, such that the desired human gene is flanked by two recombinase recognition sites. The transgene construct is subsequently introduced into the targeted animal cells resulted from the first homologous recombination event. A source of recombinase is provided to trigger the site-specific recombination that results in the exchange of the endogenous animal gene for the desired human gene. The recombinase recognition sequences may remain present in the locus after the exchange and preferably not be present in the protein-coding region.

Generating a Humanized Transgenic Animal Expressing a Plurality of Human Genes

The humanized transgenic animals expressing at least two human genes may be generated through a number of individual steps. For example, a first transgenic animal is produced from embryos or ES cells which harbor a first desired human gene. A second transgenic animal is then produced from embryos or ES cells which harbor a second desired human gene. The first transgenic animal is then crossed with the second transgenic animal to generate a transgenic animal that expresses both the first human gene and the second human gene. Similarly, a transgenic animal can be produced from embryos or ES cells in which the endogenous animal gene corresponding to the first human gene is silenced. The resulting transgenic animal can then be used to cross with the transgenic animal expressing the first human gene to produce a transgenic animal in which the first human gene operably replaces the corresponding animal gene (see, e.g., Mihara et al., Eur J Immnol 35, 2573-2582 (2005)). For anther example, a first transgenic animal can be produced from embryos or ES cells in which the first desired human gene replaces the corresponding animal gene through homologous recombination. A second transgenic animal can be produced from embryos or ES cells in which the second desired human gene replaces the corresponding animal gene through homologous recombination. The first and the second transgenic animals are subsequently bred together to generate a single animal wherein both desired animal genes are replaced by corresponding human genes.

Additionally, both the first and the second desired human genes may be introduced into a single embryo or ES cell to replace the corresponding animal genes. Once an embryo or ES cell wherein both desired animal genes are replaced by corresponding human genes are produced and selected, a transgenic animal having the same genetic alterations is created through the use of the selected embryo or ES cells.

Typically, crossing and backcrossing is performed by mating siblings or a parental strain with an offspring, depending on the goal of each particular step in the breeding process. In certain cases, it may be necessary to generate a large number of offspring in order to generate a single offspring that contains each of the desired human genes and/or the animal gene disruption. In addition, it may be necessary to cross or backcross over several generations to ultimately obtain the desired genotype.

Verification of the Presence of Transgenes

After the desired human genes are introduced into the transgenic animals, the presence and/or expression of the desired human gene in the desired cell, tissue or animal may be screened by any suitable method (see, general, Transgensis Techniques: Principles and Protocols, Clarke eds., Human Press, pp 83-90 (2002)). Standard methods to detect the presence of the desired human gene in the genome of the transgenic animal include Southern blot analysis, using a probe that is complementary to at least a portion of the transgene, and PCR analysis. Typically, genomic DNA is prepared from tail tissue and analyzed by Southern blot or PCR for the presence of the desired human gene. Alternatively, the transcriptional expression of the desired human gene can be assayed by methods include Northern blot analysis and reverse transcription polymerase chain reaction (RT-PCR). Typically, total RNA or mRNA is prepared from the tissues or cells believed to express the desired human gene at a high level and analyzed by Northern blot or RT-PCR. Further, the presence of the desired human protein can be screened by methods include Western blot analysis, using an antibody against the desired human protein. The tissues or cells believed to express the desired human protein at a high level are tested using Western blot analysis. Additional methods for evaluating the presence of the desired human protein include, without limitation, suitable biochemical assays such as histological stains for particular marker or enzyme activities, flow cytometric analysis, enzyme and/or immunological assays, and the like.

Uses of Humanized Transgenic Animals

The humanized transgenic animals of the present invention represent models of at least two human proteins interacting with each other. Accordingly, these animals are useful in studying how human proteins interact with each other and how potential molecules modulate the interaction. These animals are useful to generate and test products useful in treating and diagnosing diseases associated with the desired human genes.

In some embodiments, the desired human proteins expressed in the humanized transgenic animals retain similar functional properties as are exhibited in humans. Accordingly, the humanized transgenic animals of the invention can be utilized as models for determining whether the human protein interaction is modulated by a molecule by administering the molecule in the humanized transgenic animal and assaying the change of the human protein interaction.

The humanized transgenic animals of the present invention, including cells, tissues, or other materials derived therefrom, can also be utilized as a model for diseases associated with or mediated by the desired human genes. Animals of many species, including, but without limitations to, mice, rats, rabbits, guinea pigs, pigs, micro-pigs, goats, and non-human primates may be used to generate disease animal models. These models may be utilized, in combining with a variety of assays, as part of screening strategies designed to identify agents, such as compounds that are capable of ameliorating diseases symptoms. Therefore, the animal- and cell-based models derived from the transgenic animals of the present invention may be used to identify drugs, pharmaceuticals, therapies and interventions that may be effective in treating diseases. For example, a transgenic animal with humanized VEGF and VEGFR may be used to identify agents, such as anti-human VEGF antibodies and small molecule VEGF antagonists, capable of treating a VEGF related diseases. For another example, a transgenic animal with humanized APP and gamma-secretase may be used to identify agents inhibiting proteolytic activity of gamma-secretase and capable of treating Alzheimer's diseases.

EXAMPLES

Example I

Generation of knock-in mice expressing humanized forms of VEGF. As disclosed in Cellular, Molecular, and Tumor Biology 95: Angiogenesis Mechanisms and Microenvironment (Abstract #4782, 2004), Ajay K. Malik et al. were able to knock-in human VEGF and remove corresponding murine VEFG in mice. Briefly, Ajay K. Malik et al. describe the generation of two strains of transgenic mice expressing different forms of humanized VEGF, which are both neutralized by Avastin. The murine VEGF gene encodes 191 amino acids, 19 of which are different between mice and humans. Based on structural and biochemical data, Ajay K. Malik etl al. engineered two mutant forms, containing either one (mutI) or ten (mutX) human amino acid replacements, respectively. Biochemical analysis of recombinant protein revealed similar binding affinities between Avastin and mutI, mut X and fully human VEGF. When tested for mitogenic activity, both mutant forms displayed comparable potencies to human VEGF and Avastin blocked the biological effects of all proteins to similar degrees. Targeting vectors were generated and ES cells carrying these mutations were obtained after homologous recombination and removal of the neo-mycine selection cassette employing Cre-Lox technology. ES cell clones were characterized by Southern, PCR and sequencing analysis. Conditioned medium from positive ES cell clones were tested for the presence of humanized forms of VEGF. Comparable expression levels with mouse VEGF were identified by ELISA using the Avastin antibody. Heterozygous mice for either mutant allele are viable and are being bred to homozygosity for preclinical studies. Thus, both transgenic strains can be helpful for the evaluation of pharmacological activities of various compounds targeting human VEGF in mice.

Example II

Generation of mice expressing humanized forms of VEGF. According to Hans-Peter Gerber's group (Gerber et al., Mice expressing a humanized form of VEGF-A may provide insights into the safety and efficacy of anti-VEGF antibodies, PNAS Vol. 104, pp: 9 3478-3483 (2007)), Gerber et al. were able to knock-in humanized VEGF in mice.

It is now well established that VEGF-A is an important mediator of physiological and pathological angiogenesis. Several VEGF inhibitors have demonstrated efficacy in patients with cancer and neovascular age-related macular degeneration (AMD). Among these, the anti-VEGF-A Mab bevacizumab (AVASTIN) has been approved by the FDA for the treatment of metastatic colorectal (8) and nonsquamous, non-small-cell lung cancer, in combination with chemotherapy. Bevacizumab is a humanized variant of mouse anti-human VEGF Mab A4.6.1, which was initially identified by its ability to block human VEGF-A-stimulated endothelial cell (EC) proliferation and subsequently was shown to inhibit growth of human tumor xenografts in nude mice.

Bevacizumab and Mab A4.6.1 neutralize all isoforms of human VEGF-A and show similar Kd values toward huVEGF-A165. Mab Y0317 is an affinity-matured variant of bevacizumab. The Fab form of Y0317 (ranibizumab) was recently approved by the FDA for the treatment of neovascular AMD.

Although these Mabs block human VEGF-A, they fail to neutralize rodent VEGF-A. Therefore, their main preclinical value has been in disease models in which human VEGF-A is a key driver of angiogenesis. However, such antibodies could provide no insight into the role of host-derived VEGF in tumor angiogenesis, nor could they reveal any undesired toxicities associated with VEGF inhibition in rodents.

To overcome these limitations, Gerber et al. sought to develop mice expressing a humanized form of VEGF-A. Gerber et al. used a gene-replacement technique (gene knock-in technology) by which the mouse sequence was replaced with the human counterpart at the corresponding genomic location. Several in vitro and in vivo studies have indicated that there is little, if any, species-specificity in the effects of VEGF. Thus, we hypothesized that adult knockin mice expressing a humanized form of VEGF-A would be viable and could be used as a model to evaluate additional anti-VEGF antibodies with different epitopes and binding affinities, in either immunocompetent or immunodeficient genetic backgrounds. Such a model might be useful also to probe the role of VEGF-A in genetic cancer models in transgenic mice.

According to Gerber et al., X-ray structure, combined with site-directed mutagenesis, identified three different regions corresponding to sequences encoded by exons 3 and 4 of VEGF-A that are in direct contact with bevacizumab. The majority of these contacts are formed by residues of the β5-β6 loop (around residue 80), with two additional residues from the N-terminal helix and two residues from the α1-β32 loop (around residue 40) interacting at the margin of the interface. With the exception of one residue, all of the amino acids of human VEGF-A that are in contact with bevacizumab are conserved in mouse VEGF-A. The nonconserved residue, human Gly-88, corresponds to Ser-87 in the mouse VEGF sequence and is located in the core of the protein-antibody interface. The crystal structure of human VEGF-A in complex with the bevacizumab-Fab revealed that the interface between the molecules is tightly packed. Modeling of the serine side chain present in mouse VEGF-A, reveals that there is not enough room to accommodate the two additional nonhydrogen atoms that are introduced by the Gly-88→Ser exchange. Previous studies demonstrated that mutation of Gly-88 to alanine (Gly88A1a) in human VEGF-A substantially reduced the binding of Mab A4.6.1. These observations suggested that introducing a single mutation Ser87Gly in mouse VEGF might be sufficient to restore binding to and neutralization by A4.6.1. However, the crystal structure of the complex and the mutagenesis analysis were performed by using a truncated VEGF-A variant (8-109). Therefore, the contribution of residues not present in VEGF8-109 was unknown. Furthermore, phage derived antibodies such as G6-31 or B20-4 were known to contact additional nonconserved residues. These observations prompted us to design a more extensively humanized murine VEGF-A that could be recognized by additional antibodies. Gerber et al. therefore generated two versions of "humanized" VEGF-A proteins. One mutant containing the single Ser87Gly mutation and a second form, hum-X VEGF, in which the 10 residues that are different in the receptor-binding domain between murine and human VEGF-A are replaced by the respective amino acids in the human sequence Recombinant hum-X VEGF, WT human and murine VEGF-A proteins were expressed in Escherichia coli and purified. Gerber et al. first determined the relative affinities of bevacizumab and three second-generation anti-human VEGF antibodies for the native human VEGF-A and the hum X VEGF protein. The substitution of 10 human amino acids into the murine VEGF-A results in a protein that is recognized by all anti-human VEGF-A Mabs, with little change in affinity relative to WT human VEGF-A. Next, Gerber et al. assessed the potencies of each VEGF-A variant to stimulate proliferation of cultured EC. HuVEGF-A, muVEGF-A, and hum-X VEGF stimulated bovine capillary EC proliferation at half-maximal concentrations of 1.5, 0.6, and 0.9 ng/ml, respectively. Similar results were obtained with HUVE cells. Finally, Gerber et al. compared the potencies of the various anti-VEGF-A antibodies to interfere with EC proliferation induced by the various recombinant VEGF-A proteins. As expected, bevacizumab and Y0317 failed to block murine VEGF-A, whereas the EC50 values of the remaining ligand/antibody pairs correlated well with antibody affinities, with the exception of B20-4.1, which showed higher than expected EC50 toward murine VEGF-A. These data confirm that the hum-X, WT human, and WT mouse VEGF-A proteins have comparable biological and biochemical properties and that the ability of antibodies to interfere with the hum-X variant relative to WT human VEGF-A correlates with their respective affinities for the WT human protein.

Having established the near equivalency of hum-X VEGF and WT murine VEGF-A in vitro, Gerber et al. proceeded to generate gene-targeting vectors to introduce 1 or 10 human amino acids into the mouse germ-line. Correct recombination events in ES cells were verified by Southern blotting experiments, genomic PCR, and genomic sequencing and by determination of VEGF-A expression in targeted ES cells by ELISA. Genotype frequency analysis of >500 KI mice revealed the expected Mendelian ratios of homozygous single mutant or 10-amino acid mutant (hum-X VEGF) mice, and no change in viability and survival of adult mice during a 1 year observation period was found.

Example III

Generation of mice having knock-in fully human VEGF. Using methods disclosed in Example I and II, fully human VEGF gene can be knocked-in into mice wherein the murine VEGF counterpart is knocked-out. The presence of the gene and the expression thereof can be assessed via Southern blot, Northern blot as well as ELISA.

Example IV

Generation of mice having knock-in human VEGF receptor gene. Flk-1 (human counterpart, KDR) tyrosine kinase, which is one of the two VEGF receptors, is crucial for vascular development. Flk-1 knockout mice can be purchased from The Jackson Laboratory. Human KDR can be knocked-in the Flk-1 knockout mice using methods know in the art. For example, a target vector capable of carrying human KDR is prepared (See Sakurai et al., Essential role of Flk-1 (VEGF receptor 2) tyrosine residue 1173 in vasculogenesis in mice, PNAS vol. 102, pp. 1076-1081 (2005)). In the targeting vector, a loxP-flanked neomycin (neo) resistance gene (pMC1-NeopolyA) is inserted, and a diphtheria toxin A subunit gene (pMC1-DT-A) is inserted at the 3'terminus of the targeting vectors. The targeting vectors are linearized and transfected into 129 E14 embryonic stem (ES) cells by electroporation. ES cell clones are selected with 400 µg/ml G418 and screened by Southern blotting. The mutations of ES clones are confirmed by sequencing. Each ES cell clone correctly targeted for KDR is injected into C57BL/6J blastocysts, and the chimeras were mated with C57BL/6J females. For deletion of the neo-resistance gene, KDR heterozygous males are mated with CAG-cre transgenic females. Deletion of the neo gene is confirmed by Southern blotting. Fully human KDR heterozygous mice are then intercrossed to generate homozygous mutant mice. Mice are genotyped by Southern blotting and genomic PCR. Full-length mRNA sequences of KDR are confirmed by sequencing analysis with mRNAs from KDR homozygous embryos.

Example V

Generation of mice having human IL-3/GM-CSF knock-in genes. According to Willinger et al. (Willinger et at., Human IL-3/GM-CSF knock-in mice support human alveolar macrophage development and human immune responses in the lung, PNAS Vol. 108 (6): 2390-2395 (2011)), several mouse cytokines, such as IL-3 and GM-CSF, do not act on the human cognate receptors. In addition, Rag2−/− Il2rg−/− mice have an intact mouse myeloid compartment, and human myeloid cells might have a competitive disadvantage relative to host cells. To overcome these limitations, Willinger et al. decided to generate human cytokine knock-in (KI) mice where mouse cytokines are replaced by their human counterparts. Criteria for cytokine replacement are: (i) mouse cytokine does not or weakly act on human cells; (ii) human cytokine does not or weakly act on mouse cells to confer competitive advantage to human cells; (iii) human cytokine is not exclusively produced by hematopoietic (transplanted) cells; and (iv) lack of mouse cytokine is not lethal to mouse host or human KI cytokine is sufficiently cross-reactive to rescue the mouse knockout (KO) phenotype. The KI strategy should allow faithful expression in appropriate organs and at physiologic concentrations. Importantly, in homozygous KI mice, human cognate receptor-expressing cells should gain a competitive advantage over the respective mouse cells.

The genes encoding GM-CSF (CSF2) and IL-3 (IL3) are closely linked (<10 kb) on chromosomes 5 and 11 in humans and mice, respectively. This closeness allowed Willinger et al. to replace the mouse with the human loci for both genes to generate hIL-3/GM-CSF KI mice. Although the human IL3 KI allele is under the control of mouse regulatory elements, the human CSF2 KI allele remains under the control of its human regulatory elements. Willinger et al. analyzed expression of mouse and human GM-CSF mRNA by RT-PCR in hIL-3/GM-CSF KI mice expressing one allele of each mouse and one allele of each human gene, referred to as IL-3/GM-CSF "human/mouse" (h/m) mice. Wild-type mice that only have the mouse alleles of Il3 and Csf2 are referred to as IL-3/GM-CSF "mouse/mouse" (m/m) mice. Human GM-CSF mRNA was expressed in a similar pattern to its mouse counterpart, with highest expression in the lung. To confer a competitive advantage to human hematopoietic cells, Willinger et al. generated homozygous KI mice that express two alleles of human IL3 and CSF2, referred to as IL-3/GM-CSF "human/human" (h/h) mice. Conventional and quantitative RT-PCR analysis of lung tissue showed that h/h mice express only human, but not mouse GM-CSF mRNA. Human GM-CSF protein could be detected by ELISA in the bronchoalveolar lavage fluid of h/h mice. Both mouse and human IL-3 mRNA was highly expressed by activated splenocytes from h/m mice, with low expression in digested bone, but neither was expressed in the lung. Human IL-3 (and GM-CSF) protein could be detected in supernatants from activated splenocytes isolated from h/m mice. It was concluded that hIL-3/GM-CSF KI mice faithfully express human GM-CSF and IL-3. (See Willinger et al. PNAS Vol. 108 (6): 2390-2395 (2011)).

Example VI

Generation of mice having human GM-CSF receptor genes knocked-in. The GM-CSF receptor knockout mouse has long been available in the art (See Reed & Whitsett, Granulocyte-macrophage colony-stimulating factor and pulmonary surfactant homeostasis, Proc Assoc Am Physicians. 110(4):321-32 (1998)). The human counterpart of human GM-CSF receptor gene can then be knocked-in the GM-CSF receptor knockout mouse to make a mouse expressing fully human GM-CSF receptor.

Example VII

Generation of mice expressing two interacted human proteins. The humanized or human VEGF knocked-in mice are bred with the human VEGF-receptor (KDR) knocked-in mice. Off-springs are examined to identify the ones expressing human or humanized VEGF and VEGF-receptor. By the same token, hIL-3/GM-CSF KI mice faithfully express human GM-CSF and IL-3 are bred with mice expressing human GM-CSF receptor to produce off springs that express human GM-CSF and IL-3 and GM-CSF receptor.

Example VIII

Evaluation of mice expressing two interacted human proteins. Mice that express human or humanized VEGF and VEGF-receptor are injected with bevacizumab (Avastin). It is observed that bevacizumab blocks the interaction between human or humanized VEGF and human VEGF receptor in mice.

What is claimed is:
1. A humanized transgenic animal comprising a first human gene encoding a first human protein and a second human gene encoding a second human protein,
   wherein the first human protein and the second human protein directly interacts with each other in transducing signals from the exterior of a cell,
   wherein the direct interaction between the first human protein and the second human protein is without the presence of a third protein,
   wherein a first animal gene substantially homologous to the first human gene in the transgenic animal genome is replaced by the first human gene and a second animal gene substantially homologous to the second human gene in the transgenic animal genome is replaced by the second human gene, and the human genes are wild type human genes, and are operably linked to the transcriptional regulatory sequences of the endogenous animal genes, and
   wherein the animal is mouse or rat.

2. A method of evaluating whether a molecule modulates human protein interaction in an animal comprising the steps of administering the molecule in a humanized transgenic animal of claim 1 and determining whether the human protein interaction is modulated.

3. A humanized transgenic animal comprising a first human gene encoding a first human protein and a second human gene encoding a second human protein,
   wherein the first human protein and the second human protein directly interacts with each other in transducing signals from the exterior of a cell,
   wherein the direct interaction between the first human protein and the second human protein is without the presence of a third protein,
   wherein a first animal gene substantially homologous to the first human gene in the transgenic animal genome is replaced by the first human gene and a second animal gene substantially homologous to the second human gene in the transgenic animal genome is replaced by the second human gene, and the human genes are wild type human genes, and are operably linked to transcriptional regulatory sequences of the endogenous animal genes,
   wherein the first human protein and the second human protein is a pair of proteins selected from the group consisting of (i) VEGF and VEGF receptor; (ii) GM-CSF and GM-CSF receptor; and (iii) mitogen-activated protein (MAP)-kinase-kinase and MAP-kinase, and
   wherein the animal is mouse or rat.

4. The humanized transgenic animal of claim 3, wherein the first human protein and the second human protein is a pair of proteins selected from the group consisting of (i) VEGF and VEGF receptor; and (ii) GM-CSF and GM-CSF receptor.

5. The humanized transgenic animal of claim 3, wherein the first human protein and the second human protein are VEGF and VEGF receptor, respectively.

6. A method of evaluating whether a molecule modulates human protein interaction in an animal comprising the steps of administering the molecule in a humanized transgenic animal of claim 3 and determining whether the human protein interaction is modulated.

\* \* \* \* \*